United States Patent
Ho et al.

(10) Patent No.: US 8,609,429 B2
(45) Date of Patent: Dec. 17, 2013

(54) METHODS FOR IDENTIFYING HIGH FOULING HYDROCARBON AND FOR MITIGATING FOULING OF PROCESS EQUIPMENT

(75) Inventors: Teh C. Ho, Bridgewater, NJ (US); Glen B. Brons, Phillipsburg, NJ (US); Limin Song, West Windsor, NJ (US); Tahmid I. Mizan, Coppell, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 244 days.

(21) Appl. No.: 13/299,178

(22) Filed: Nov. 17, 2011

(65) Prior Publication Data

US 2012/0122230 A1    May 17, 2012

Related U.S. Application Data

(60) Provisional application No. 61/421,700, filed on Dec. 10, 2010, provisional application No. 61/414,669, filed on Nov. 17, 2010.

(51) Int. Cl.
   *G01N 25/20* (2006.01)
(52) U.S. Cl.
   USPC ............... 436/147; 208/18; 208/19; 208/48 R
(58) Field of Classification Search
   None
   See application file for complete search history.

(56) References Cited

U.S. PATENT DOCUMENTS

| 4,766,553 A | 8/1988 | Kaya et al. |
| 2009/0032435 A1 | 2/2009 | Brons et al. |

FOREIGN PATENT DOCUMENTS

| FR | 2885694 A1 | 11/2006 |
| WO | 200007000 A1 | 2/2000 |

OTHER PUBLICATIONS

Srinivasan et al., "Fouling of Some Canadian Crude Oils", Heat Transfer Engineering, Hemisphere Pub., Washington, DC, US, vol. 26, No. 1 (Jan. 1, 2005), pp. 7-14.
PCT/US2011/062830, Aug. 2, 2012, Search Report.
PCT/US2011/062830, Aug. 2, 2012, Written Opinion.

*Primary Examiner* — Robert Xu
(74) *Attorney, Agent, or Firm* — Glenn T. Barrett

(57) ABSTRACT

Methods for determining the fouling propensity of a hydrocarbon stream and for reducing fouling are provided. In one method, the fouling propensity of a hydrocarbon stream is determined by obtaining a parameter value indicative of the fouling propensity at no less than two different temperatures, and an activation energy of fouling by the hydrocarbon stream is derived therefrom. In another method, the thus obtained parameter value at no less than two different temperatures and the activation energy are used to select proper heating fluids and operating temperature and to determine whether to add an antifoulant to the hydrocarbon stream to reduce fouling at a given temperature.

14 Claims, 2 Drawing Sheets

METHODS FOR IDENTIFYING HIGH FOULING HYDROCARBON AND FOR MITIGATING FOULING OF PROCESS EQUIPMENT

CROSS REFERENCE TO RELATED APPLICATIONS

This application relates and claims priority to U.S. Provisional Patent Application No. 61/421,700, filed on Dec. 10, 2010.

This application relates to U.S. Provisional Application No. 61/414,669, entitled "Methods for Mitigating Fouling of Process Equipment", filed on Nov. 17, 2010, the disclosure of which is incorporated by reference in its entirety.

FIELD OF THE INVENTION

The presently disclosed subject matter relates to methods for determining the sensitivity of fouling propensity of hydrocarbon streams to temperature change, as well as for reducing and mitigating fouling of process equipment by the hydrocarbon streams.

BACKGROUND OF THE INVENTION

The deposition of organic and/or inorganic foulants on process equipment accounts for a significant amount of energy loss in oil production, refining and chemicals manufacturing. For example, the thermal processing of crude oils, blends and fractions in heat transfer equipment, such as heat exchangers, is hampered by the deposition of insoluble asphaltenes and other contaminants (i.e., particulates, salts, etc.) that may be found in crude oils. Further, the asphaltenes and other organics may thermally degrade to coke when exposed to high heater tube surface temperatures.

The most common heat exchanger in oil refineries and petrochemical processes is the shell-and-tube type, which consists of a shell with a bundle of tubes inside it. The crude oil runs through the tubes, and the heating fluid flows over the tubes (through the shell) to transfer heat to the crude oil through the tube/shell walls. Typically, the heating fluid is a petroleum fraction with a specific boiling range, which in general comes from a side stream of the vacuum or atmospheric pipe still. If the heating fluid is a heavy (high boiling) fraction, the operating temperature is high compared to that used with a light (low boiling) fraction.

Fouling in heat exchangers receiving hydrocarbon process streams can result from a number of mechanisms including chemical reactions, corrosion, deposit of existing insoluble impurities in the stream, and deposit of materials rendered insoluble by the temperature difference between the process stream and the heat exchanger wall. For example, naturally-occurring asphaltenes can precipitate from the crude oil process stream, thermally degrade to form a coke and adhere to the hot surfaces. Further, the high temperature difference found in heat transfer operations result in high surface or skin temperatures when the process stream is introduced to the heater tube surfaces, which contributes to the precipitation of insoluble particulates. Another common cause of fouling is attributable to the presence of salts, particulates and impurities (e.g. inorganic contaminants) found in the crude oil stream. For example, iron oxide/sulfide, calcium carbonate, silica, sodium chloride and calcium chloride have all been found to attach directly to the surface of a fouled heater rod and throughout the coke deposit. These solids promote and/or enable additional fouling of crude oils. The fouling propensities of different hydrocarbon streams (such as crude oils or refinery process streams) may vary considerably. Under the same operating conditions, some streams foul easily, while other streams may experience minimal fouling.

The buildup of insoluble deposits in heat transfer equipment, such as a heat exchanger, creates an unwanted insulating effect, reduces the heat transfer efficiency and increases energy consumption. Fouling also reduces the cross-sectional area of process equipment, which decreases flow rates and desired pressure differentials to provide less than optimal operation. As a result, heat transfer equipment is ordinarily taken offline and cleaned either mechanically or chemically, resulting in lost production time. In many cases, fouling even causes unwanted and unexpected shutdowns.

Great strides have been made to develop antifoulant agents, additives or coatings. While the addition of antifoulant additives leads to significant energy savings, it introduces attendant costs, including the cost of the additive itself and the cost of removing the additive from the process downstream. As such, it is vitally important to minimize the amount of additive that is introduced to the process while achieving the desired level of fouling reduction, i.e., using only the minimally required level of additive to achieve effective fouling prevention. This requires the development of an accurate and sensitive way of a priori prediction of the fouling propensity of an oil so that an optimal dosage of the additive can be estimated and applied. As well, the fouling propensity can be used as a basis for selecting, purchasing, and blending various hydrocarbon streams to achieve effective fouling prevention.

Furthermore, as fouling is often sensitive to the processing temperature of the hydrocarbon stream, it would be useful to develop a way to determine a priori the temperature sensitivity of fouling by a hydrocarbon, which can not only help predict the fouling propensity of a hydrocarbon but also help select operating conditions so that fouling can be avoided or minimized.

SUMMARY

The disclosed subject matter provides a method for determining temperature sensitivity related to the propensity of a hydrocarbon stream to foul process equipment is disclosed. The method includes:

(a) introducing a hydrocarbon stream to a test unit, the test unit comprising a chamber defined by a wall for the hydrocarbon to flow through, an inlet for feeding the hydrocarbon into the chamber, an outlet to discharge the hydrocarbon stream, and a heating element maintained at a substantially constant surface temperature Tc and disposed within the chamber to heat the hydrocarbon flowing across the surface of the heating element to cause fouling;

(b) obtaining a series of temperature measurements over time of the hydrocarbon stream exiting the outlet of the test unit, including: (1) measuring an initial temperature $T_1$ of the hydrocarbon exiting from the outlet when the heating element is substantially free from fouling; (2) measuring the temperature $T(t)$ of the hydrocarbon exiting from the outlet successively at predetermined time intervals subsequent to measuring the initial temperature $T_1$, where t denotes time; and (c) determining a parameter value indicative of a propensity of the hydrocarbon to foul process equipment by a regression of ΔT(t) according to function:

$$\Delta T(t) = 1 - \left[ \frac{1 + \sigma(ut/L - 1)}{(1 - \sigma)(1 + \sigma ut/L)} \right]^{1/(\sigma P)}$$

where ΔT(t) is a time-dependent quantity defined as ΔT(t)= [T(t)−$T_1$]/($T_c$−$T_1$), σ is the fouling parameter value at surface temperature of the heated element Tc, which is also referred to as Fouling Susceptibility Index, or FSI. Also, t is time, u is the average velocity of the hydrocarbon in the chamber of the test unit, and P is a factor relating to heat transfer;

(d) repeating steps (a)-(c) at a second and different surface temperature of the heating element Tc to obtain a second fouling parameter value corresponding to the second temperature of the surface of the heated element;

(e) deriving an activation energy Ea of the fouling by the hydrocarbon stream from the data obtained at the above-mentioned two temperatures based on the Arrhenius principle, which states that the slope of the ln σ vs 1/Tc linear plot is the fouling activation energy;

(f) if desired, repeating steps (a)-(d) at a third and different surface temperature of the heating element Tc to obtain a third fouling parameter value at the third temperature of the surface of the heated element; and (e) deriving an activation energy Ea of the fouling by the hydrocarbon stream from the data obtained at the above-mentioned three temperatures based on the Arrhenius principle via a least-squares type of regression procedure.

Based on the fouling parameter values, or the FSIs, obtained at no less than two different surface temperatures of the heated element according to the above described method, the disclosed subject matter further provides a method for determining the activation energy for the fouling process. The thus-determined activation energy is then used to guide the selection of (1) a hydrocarbon stream, (2) the heating fluid, and (3) the appropriate operating temperature for processing the hydrocarbon stream to reduce fouling.

DETAILED DESCRIPTION

Figure 1:
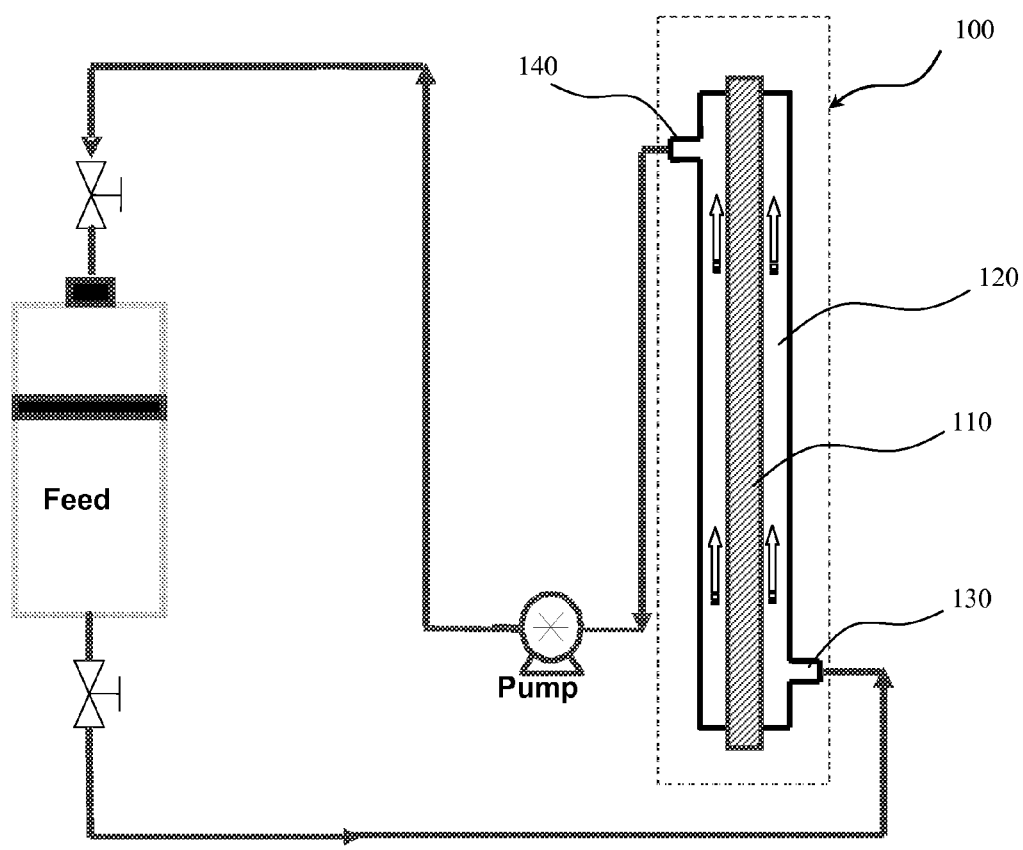
FIG. 1 depicts an exemplary structure of the test unit used according to some embodiments of the presently disclosed subject matter.

The disclosed subject matter provides a method for determining temperature sensitivity related to propensity of a hydrocarbon stream to foul process equipment. In accordance with the present invention, the terminology "hydrocarbon stream" is intended to include, but is not limited to hydrocarbon streams that may contain heteroatoms, metals, particulates, salt, some water, and biomaterials. The method includes:

(a) introducing a hydrocarbon stream to a test unit, the test unit comprising a chamber defined by a wall for the hydrocarbon to flow through, an inlet for feeding the hydrocarbon into the chamber, an outlet to discharge the hydrocarbon stream, and a heating element maintained at a substantially constant surface temperature Tc and disposed within the chamber to heat the hydrocarbon flowing across the surface of the heating element to cause fouling;

(b) obtaining a series of temperature measurements over time of the hydrocarbon stream exiting the outlet of the test unit, including: (1) measuring an initial temperature $T_1$ of the hydrocarbon exiting from the outlet when the heating element is essentially free from fouling; (2) measuring the temperature T(t) of the hydrocarbon exiting from the outlet successively at predetermined time intervals subsequent to measuring the initial temperature $T_1$, where t denotes time;

(c) determining a parameter value indicative of a propensity of the hydrocarbon to foul process equipment by a regression of ΔT(t) according to the following equation:

$$\Delta T(t) = 1 - \left[ \frac{1 + \sigma(ut/L - 1)}{(1 - \sigma)(1 + \sigma ut/L)} \right]^{1/(\sigma P)}$$

where ΔT(t) is a time-dependent quantity which is defined as ΔT(t)=[T(t)−$T_1$]/($T_c$−$T_1$), σ, the FSI, is the dimensionless fouling parameter value at heating element temperature Tc, t is time, u is the average velocity of the hydrocarbon in the chamber of the test unit, and P is a dimensionless parameter relating to the system's heat transfer capacity (It should be noted that through regression of the ΔT(t) function, both parameters σ and P can be extracted simultaneously);

(d) repeating steps (a)-(c) at a second and different surface temperature of the heating element Tc to obtain the value of σ at the second temperature of the surface of the heated element;

(e) deriving an activation energy Ea of the fouling by the hydrocarbon stream from the data obtained at the above-mentioned two temperatures based on the Arrhenius principle, which states that the slope of the lnσ vs, 1/Tc linear plot is the fouling activation energy;

(f) if desired, repeating steps (a)-(d) at a third and different surface temperature of the heating element Tc to obtain a third fouling parameter value at the third temperature of the surface of the heated element; and (g) deriving an activation energy Ea of the fouling by the hydrocarbon stream from the data obtained at the above-mentioned three temperatures based on the Arrhenius principle via a least-squares type of regression analysis.

It should be noted that a more accurate determination of the activation energy can be achieved by repeating the above steps at three or more temperature levels. The present invention is not intended to be limited to the determination of the activation energy at three temperature levels; rather, it is contemplated various temperature levels are within the scope of the present invention.

Based on the determined parameter value at no less than two different surface temperatures of heated element according to the above described method, the disclosed subject matter further provides a method to determine the existence of a need to add an antifoulant to the hydrocarbon stream to reduce fouling at an another temperature, as well as a method to determine an appropriate heating fluid and the associated operating temperature for processing the hydrocarbon stream to reduce fouling. It is possible to determine which crude oils will foul at a given temperature, which crude oils have a higher propensity to foul when compared to other crude oils, and the operating temperature at which the crude oils may be used in order to avoid fouling.

For purpose of illustration, reference is made to a test unit suitable for conducting a series of temperature measurements of the hydrocarbon stream of interest exiting from the test unit. One example of such a test unit is an Alcor Hot Liquid Process Simulator (HPLS) commonly used in the oil industry. The Alcor HPLS has been commonly used for measuring the fouling behavior of oils. As depicted in FIG. 1, the test unit 100 includes a heated rod 110, a tubular chamber 120, an inlet 130 and an outlet 140 disposed at opposing ends of the tubular chamber 120. A hydrocarbon stream can be introduced to the chamber at a constant feed temperature and flow rate into the inlet, flows through the chamber and across the surface of the heated rod which is maintained at a constant surface temperature Tc, and then exits the chamber via the outlet 140. The feed temperature of the hydrocarbon can be in the range of 100-150° C., and are typically lower than the rod temperature which is ranged from about 300° C. to 500° C. Heat is transferred from the rod (which simulates a heat exchanger) to the hydrocarbon stream (e.g., a crude oil or oil blend), and as a result, fouling may occur on the surface of the heated rod which will gradually decrease the heat transfer efficiency from the rod to the hydrocarbon stream. The present invention is not intended to be limited for use with the Alcor HPLS; rather, other testing devices capable of obtaining temperature measurements of a sample process stream are considered to be well within the scope of the present invention.

To quantify the effect and severity of the fouling, a series of temperature measurements can be made as hydrocarbon stream exits the test unit. In the presently disclosed subject matter, the entire profile of the temperature versus time is considered, and employed to derive a useful parameter, i.e., FSI, from data regression techniques based on a mathematical formula. A series of successive temperature measurements can be taken subsequent to the measurement of $T_1$. A normalized (hence dimensionless) temporal temperature is defined as $$\Delta T(t) = [T(t) - T_1]/(T_c - T_1) \quad (1)$$

As described herein, this temporal data $\Delta T(t)$ is then regressed to obtain a single parameter that reflects the intrinsic fouling propensity of the hydrocarbon in question. Specifically, $\Delta T(t)$ can be described by the following expression:

$$\Delta T(t) = 1 - \left[ \frac{1 + \sigma(ut/L - 1)}{(1 - \sigma)(1 + \sigma ut/L)} \right]^{1/(\sigma P)} \quad (2)$$

where the dimensionless parameter $\sigma$ is the FSI, which plays the pivotal role in controlling the shape of the $\Delta T(t)$ function, u and L are the average velocity of the hydrocarbon and the length of the section of the chamber where the hydrocarbon is heated, respectively. The dimensionless parameter P carries the information on system's heat transfer capacity. Through regression of the $\Delta T(t)$ function, both parameters $\sigma$ and P can be extracted simultaneously. For a group of similar hydrocarbons (e.g., crude oils), the thus-determined $\sigma$ (or FSI) can be used to quantitatively rank the fouling tendency of the oils at a given temperature. The higher the FSI, the greater is the tendency of the crude oil to foul. In the chart illustrated in FIG. 2, crude oil A has the highest FSI, which translates into the highest propensity to foul. It should be noted that the FSI generally increases with increases in temperature. It should also be noted that the FSI for one crude oil that is higher than the FSI for another crude oil at the same temperature may not higher at all temperatures (e.g., compare Crude B and Crude C or Crude D and Crude E in FIG. 2).

Figure 2:
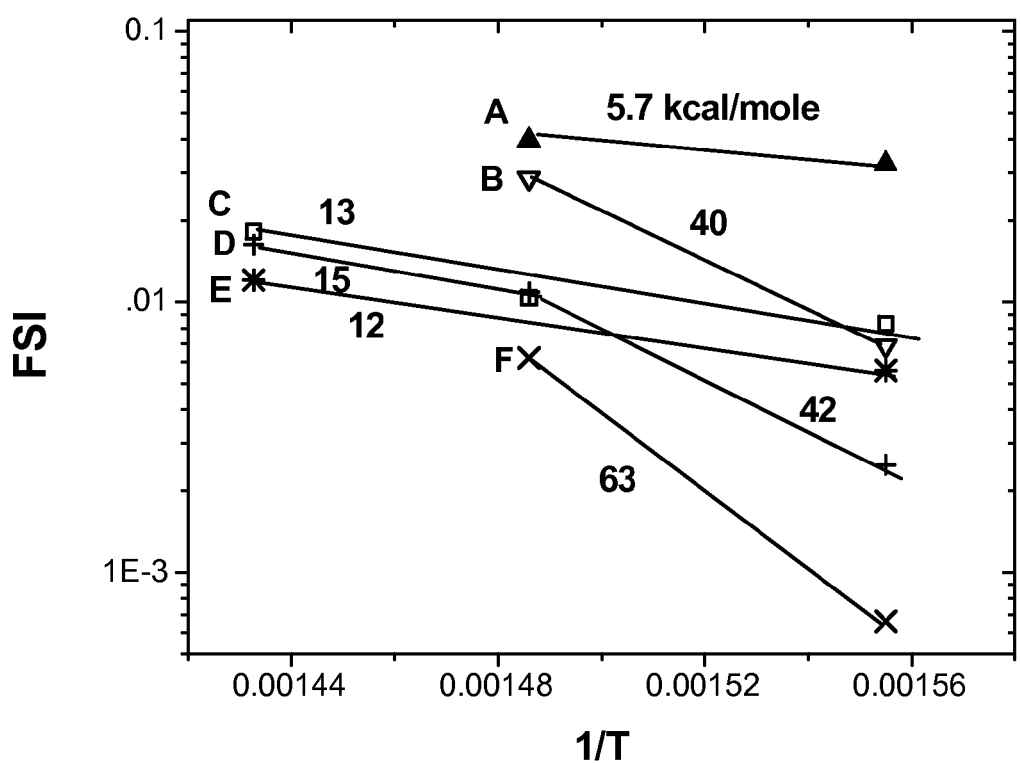
FIG. 2 is a plot for determining the temperature sensitivity of the fouling propensity of a hydrocarbon stream according to some embodiments of the presently disclosed subject matter.

The above procedure can be repeated using the same test unit at a second heated rod surface temperature to obtain a second FSI at a different temperature. The thus-obtained FSIs at two different temperatures can be used to obtain an activation energy Ea based on Arrhenius principle by plotting the two FSIs in logarithmic scale against the reciprocal of the two temperatures (denoted by the subscripts 1 and 2) in Kelvin, that is, plotting ln $(FSI_1)$ vs $1/Tc_1$ and $\ln(FSI_2)$ vs. $1/Tc_2$ and obtaining the slope of the straight line formed therefrom. As an example, FIG. 2 shows that the activation energies for Crude A and Crude B are 5.7 kcal/mole and 40 kcal/mole, respectively. Crude F is super sensitive to temperature, with an activation energy of 63 kcal/mole. Similarly, a third, fourth, or more tests could be run for the hydrocarbon stream at a third, fourth, or other rod surface temperatures, whereby multiple FSIs at different temperatures can be obtained. The logarithms of these FSIs can be related to the reciprocal of the respective temperatures (in Kelvin) according to the Arrhenius law, and fitted by linear regression to obtain the activation energy for fouling by the hydrocarbon stream.

The activation energy thus derived can be used, in conjunction with the value of the FSIs obtained at the first and the second heated element surface temperatures, to determine whether there is a need to add an antifoulant to the hydrocarbon stream to reduce fouling at a third temperature. For example, the FSI at the third temperature can be estimated from the FSIs of the first two heated element surface temperatures and the activation energy determined. Based on this predicted FSI, a decision can be made whether or not adding an antifoulant would be necessary to reduce fouling by the hydrocarbon. If the FSI is above a desired threshold at a higher temperature, it may be desirable to add an anti-foulant (e.g., an additive or an High-Solvency-Dispersive-Power (HSDP) crude oil or resin) into the crude oil in order to reduce or prevent fouling. If the FSI is below a desired threshold at a higher temperature, then there is no need to add an anti-foulant. Alternatively, Ea and FSIs obtained at the two different heated element surface temperatures can be used to determine an appropriate temperature for processing the hydrocarbon stream such that fouling is reduced or minimized. As shown in FIG. 2, the plot for a given crude oil may be used to predict at what temperature fouling would occur such that an appropriate temperature can be selected to avoid fouling. Similarly, it can be used to determine when to switch, blend with or use other crude oils in order to avoid fouling. The appropriate temperature then helps select the proper heating fluid on the shell side of a heat exchanger.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Determination of FSI in Accordance with the First Aspect Disclosed Herein

A total of six crude oils were tested in this study. They are designated as A, B, C, D, E, and F. The rod temperatures used were 370° C., 400° C., and 425° C. The relation between $\Delta T(t) \sim t$ for these crude oil samples at different heated rod surface temperatures was obtained by the procedure described above, from which the FSIs can be obtained according to Eq. 2. FIG. 2 depicts FSI (in logarithmic scale) vs. $1/T_c$. The slope of the Arrhenius plot yields the activation energies $E_a$ which reveals whether the fouling process is controlled by coking kinetics or mass transfer. If the mass transfer is controlling, this means that the oil may contain a high level of particulates or sulfur species, which diffuse from the bulk liquid to the metal surface. As can be seen from FIG. 2, Crude A has the highest FSI with the lowest Ea of 5.7 kcal/mole, suggesting a mass-transfer-controlled regime. Upon measurement, Crude A indeed has the highest level of particulates among the oils tested. This high-fouling oil would benefit from using anti-foulant additives or co-blending with an HSDP crude oil as disclosed for example in commonly assigned U.S. patent application Ser. No. 12/222,760 entitled "High-Solvency-Dispersive-Power (HSDP) Crude Oil Blending for Fouling Mitigation and On-Line Cleaning" and U.S. patent application Ser. No. 12/222,761, entitled "Mitigation of Refinery Process Unit Fouling Using High Solvency Dispersive Power (HSDP) Resid Fractions." Due to its low $E_a$, fouling of this crude oil is insensitive to temperature so a high-boiling heating fluid and hence a high operating temperature may be used to advantage. With reference to FIG. 2, fouling for those crude oil plots having a low slope hence low Ea is typically insensitive to temperature (e.g., crude oil A). Fouling for those crude oil plots with higher slopes and hence higher Ea's is more temperature dependent.

At the other end of the spectrum, Crude F gives the highest activation energy of 63 kcal/mole, indicative of a kinetics-controlled regime. That is, the underlying process is chemical in origin. While this crude would not foul at 400° C. due to its low FSI, it may foul at high temperatures. If the plot for Crude F were extended to 425° C., the predicted FSI may be higher than those for Crudes C, D and E. Crude F may have a greater propensity to foul at that temperature. Crudes C and E both show an intermediate behavior, with $E_a$=12 and 13 kcal/mole, respectively. Crude D exhibits a composite behavior in that $E_a$=42 kcal/mole at low temperatures and $E_a$=15 kcal/mole at high temperatures. This behavior indicates a change of fouling mechanism. At low temperatures, the fouling is governed by coking kinetics; at high temperatures, mass transfer becomes dominant.

The present invention is not to be limited in scope by the specific embodiments described herein. Various modifications of the invention in addition to those described herein will become apparent to those skilled in the art from the foregoing description and the accompanying figures. Such modifications are intended to fall within the scope of the appended claims.

The invention claimed is:

1. A method for determining temperature sensitivity related to propensity of a hydrocarbon stream to foul process equipment, comprising:
  a. introducing a hydrocarbon stream to a test unit, the test unit comprising a chamber defined by a wall for the hydrocarbon to flow through, an inlet for feeding the hydrocarbon into the chamber, an outlet to discharge the hydrocarbon stream, and a heating element maintained at a substantially constant surface temperature Tc and disposed within the chamber to heat the hydrocarbon flowing across the surface of the heating element to cause fouling;
  b. obtaining a series of temperature measurements over time of the hydrocarbon stream exiting the outlet of the test unit, including:
    1) measuring an initial temperature $T_1$ of the hydrocarbon exiting from the outlet when the heating element is essentially free from fouling;
    2) measuring the temperature T(t) of the hydrocarbon exiting from the outlet successively at predetermined time intervals subsequent to measuring the initial temperature $T_1$, where t denotes time;
  c. determining a parameter value indicative of a propensity of the hydrocarbon to foul process equipment by a regression of $\Delta T(t)$ according to the following expression:

$$\Delta T(t) = 1 - \left[\frac{1 + \sigma(ut/L - 1)}{(1 - \sigma)(1 + \sigma ut/L)}\right]^{1/(\sigma P)}$$

where $\Delta T(t)$ is a time-dependent quantity which is defined as $\Delta T(t) = [T(t) - T_1]/(T_c - T_1)$, $\sigma$ is the fouling parameter value at surface temperature of the heated element Tc, t is time, u is the average velocity of the hydrocarbon in the chamber of the test unit, L is the length of the section of the chamber, and P is a factor relating to heat transfer;
  d. repeating steps (a)-(c) at a second and different surface temperature of the heating element to obtain a fouling parameter value at the second temperature of the surface of the heated element;
  and
  e. determining the activation energy Ea of the fouling by the hydrocarbon stream based on the Arrhenius principle using the determined fouling parameters obtained at the first and second temperatures.

2. The method according to claim 1, further comprising: repeating steps (a)-(d) at at least one additional different surface temperature of the heating element to obtain a fouling parameter value for each additional different surface temperature.

3. The method according to claim 2, wherein determining the activation energy Ea further includes using the determined fouling parameter value for each additional surface temperature.

4. The method of claim 1, wherein the heating element of the test unit is a heated rod.

5. The method of claim 4, wherein P is a factor relating to heat transfer capacity of the system comprising the test unit wall, the heated rod, and the hydrocarbon stream.

6. The method of claim 4, wherein the constant surface temperature of the heated rod is in a range of from about 300° C. to about 500° C.

7. The method of claim 1, wherein the chamber of the test unit is tubular, and wherein the inlet and the outlet are disposed near the opposing ends of the tubular chamber.

8. The method of claim 1, wherein the hydrocarbon is maintained at a constant predetermined flow rate in the chamber of test unit.

9. The method of claim 1, wherein the hydrocarbon is at least one of a crude oil, a blend of crude oils, or a refinery process stream.

10. A method for determining whether to add an antifoulant to a hydrocarbon stream to reduce fouling, comprising:
  performing the method of claim 1 to obtain (A) a parameter value cy indicative of the propensity of the hydrocarbon to cause fouling at each of at least two different temperatures of the surface of the heated element, and (B) the activation energy of the fouling by the hydrocarbon; and determining whether to add an antifoulant to the hydrocarbon stream to reduce fouling at a third temperature based on the determined parameter value at the first and second temperatures of the surface of the heated element and the activation energy.

11. A method for determining whether to add an antifoulant to a hydrocarbon stream to reduce fouling, comprising:

performing the method of claim 3 to obtain (A) a parameter value cy indicative of the propensity of the hydrocarbon to cause fouling at no less than two different temperatures of the surface of the heated element, and (B) the activation energy of the fouling by the hydrocarbon; and determining whether to add an antifoulant to the hydrocarbon stream to reduce fouling at a third temperature based on the determined parameter value at different temperatures of the surface of the heated element and the activation energy.

12. A method for determining an appropriate temperature for processing a hydrocarbon stream to reduce fouling, comprising:

performing the method of claim 1 to obtain (A) a parameter value cy indicative of the propensity of the hydrocarbon to cause fouling at each of at least two different temperatures of the surface of the heated element, and (B) the activation energy of the fouling by the hydrocarbon; and determining the appropriate temperature for processing the hydrocarbon stream to reduce fouling based on the determined parameter value and the activation energy.

13. A method for determining an appropriate temperature for processing a hydrocarbon stream to reduce fouling, comprising:

performing the method of claim 3 to obtain (A) a parameter value cy indicative of the propensity of the hydrocarbon to cause fouling at no less than two different temperatures of the surface of the heated element, and (B) the activation energy of the fouling by the hydrocarbon; and determining the appropriate temperature for processing the hydrocarbon stream to reduce fouling based on the determined parameter value and the activation energy.

14. A method for determining an proper heating fluid for heat exchanger for heating a hydrocarbon stream with minimum fouling, comprising:

performing the method of claim 1 to obtain (A) a parameter value cy indicative of the propensity of the hydrocarbon to cause fouling at no less than two different temperatures of the surface of the heated element, and (B) the activation energy of the fouling by the hydrocarbon; and determining the proper heating fluid for processing the hydrocarbon stream to reduce fouling based on the determined parameter value and the activation energy.

* * * * *